(12) United States Patent  (10) Patent No.: US 10,744,034 B2
Homer  (45) Date of Patent: Aug. 18, 2020

(54) METHOD FOR LASER TREATMENT FOR GLAUCOMA

(76) Inventor: Gregg S. Homer, Laguna Beach, CA (US)

( * ) Notice: Subject to any disclaimer, the term of this patent is extended or adjusted under 35 U.S.C. 154(b) by 0 days.

(21) Appl. No.: 13/456,111

(22) Filed: Apr. 25, 2012

(65) Prior Publication Data

US 2013/0289450 A1 Oct. 31, 2013

(51) Int. Cl.
A61F 9/008 (2006.01)
A61N 7/00 (2006.01)
A61B 18/14 (2006.01)

(52) U.S. Cl.
CPC .......... *A61F 9/008* (2013.01); *A61F 9/00821* (2013.01); *A61F 9/00825* (2013.01); *A61B 18/14* (2013.01); *A61F 2009/00846* (2013.01); *A61F 2009/00868* (2013.01); *A61F 2009/00876* (2013.01); *A61F 2009/00891* (2013.01); *A61N 7/00* (2013.01)

(58) Field of Classification Search
CPC ....... A61N 7/00; A61H 23/0245; A61F 9/008; A61F 9/00825; A61F 9/00821; A61F 2009/00846; A61F 2009/00868; A61F 2009/00876; A61F 2009/00891; A61B 18/14
USPC .......................................................... 601/2
See application file for complete search history.

(56) References Cited

U.S. PATENT DOCUMENTS

| 3,828,788 A | 8/1974 | Karanov et al. |
| 4,391,275 A | 7/1983 | Fankhauser et al. |
| 4,791,927 A | 12/1988 | Menger |
| 4,907,586 A | 3/1990 | Bille et al. |
| 5,152,760 A | 10/1992 | Latina |
| 5,259,380 A | 11/1993 | Mendes et al. |
| 5,370,641 A | 12/1994 | O'Donnell, Jr. |
| 5,372,595 A | 12/1994 | Gaasterland et al. |
| 5,431,646 A | 7/1995 | Vassiliadis et al. |
| 5,549,596 A | 8/1996 | Latina |
| 5,549,598 A | 8/1996 | O'Donnell, Jr. |
| 6,059,772 A | 5/2000 | Hsia et al. |
| 6,220,247 B1 | 4/2001 | Maldonado |
| 6,319,274 B1 | 11/2001 | Shadduck |
| 6,514,241 B1 | 2/2003 | Hsia et al. |

(Continued)

FOREIGN PATENT DOCUMENTS

| AU | 2012261645 A1 | 1/2013 |
| RU | 2223083 C1 | 10/2004 |
| RU | 2346677 C1 | 2/2009 |

OTHER PUBLICATIONS

Latina, et al., Laser Sclerostomy by Pulsed-Dye Laser and Goniolens, Arch. Ophthalmol. (1990) 108:1745-1750.

(Continued)

*Primary Examiner* — Hien N Nguyen

(57) ABSTRACT

Because vision loss in most forms of glaucoma is related to elevated IOP, most glaucoma treatment protocols are concerned with lowering IOP by increasing aqueous humor outflow. The invention utilizes electromagnetic radiation to create retraction in the iris tissue, thereby (a) reducing convexity and enlarging the drainage angle and thus the area of the anterior chamber, (b) reducing contact between the zonule fibers and the iris pigment epithelium, (c) applying greater tension to both the TM and uveoscleral outflow pathways, thereby enlarging those pathways and increasing outflow.

13 Claims, 20 Drawing Sheets

(56) References Cited

U.S. PATENT DOCUMENTS

| | | | |
|---|---|---|---|
| 7,282,046 | B2 | 10/2007 | Simon |
| 8,230,866 | B2 | 7/2012 | Hauger et al. |
| 2002/0167644 | A1* | 11/2002 | Pollack et al. ............... 351/219 |
| 2003/0069566 | A1* | 4/2003 | Williams et al. ............... 606/5 |
| 2003/0109907 | A1 | 6/2003 | Shadduck |
| 2004/0215175 | A1* | 10/2004 | Feklistov et al. ............... 606/4 |
| 2005/0043722 | A1* | 2/2005 | Lin ............................... 606/6 |
| 2005/0049584 | A1* | 3/2005 | Homer ........................... 606/33 |
| 2007/0093794 | A1 | 4/2007 | Wang et al. |
| 2007/0161981 | A1 | 7/2007 | Sanders et al. |
| 2010/0016395 | A1* | 1/2010 | Benozzi ....................... 514/397 |
| 2010/0310637 | A1* | 12/2010 | Abdulrazik ................... 424/450 |
| 2010/0324543 | A1 | 12/2010 | Kurtz et al. |
| 2013/0103011 | A1 | 4/2013 | Grant et al. |

OTHER PUBLICATIONS

Latina, et al., Experimental Ab Interno Sclerotomies Using a Pulsed-Dye Laser, Lasers Surg. & Med.(1988) 8:233-240.

Latina, et al., Transscleral Cyclophotocoagulation Using a Contact Laser Probe: A Histologic and Clinical Study in Rabbits, Lasers Surg. & Med. (1989) 9:465-470.

Melamed, et al., Internal Sclerostomy Using Laser Ablation of Dyed Sclera in Refractory Glaucoma, Brit. J. Opthalmol. (1993) 77:181-189.

Ozler, et al., Infrared Laser Sclerostomies, Investig. Ophthalmol. & Vis. Sci. (1991) 32(9):2498-2503.

Ritch, et al., Argon Laser Peripheral Iridoplasty, Ophthalmol. Surg. & Lasers (1996) 27:289.

Robin, et al., Q-Switched Neodymium-YAG Laser Angle Surgery in Open-Angle Glaucoma, Arch. Ophthalmol (1985) 103: 793-795.

Senft, et al., Neodymium-YAG Laser Goniotomy vs Surgical Goniotomy, Arch. Ophthalmol. (1989) 107:1773-1776.

Van der Zypen, et al., The Ultrastructural Features of Laser Trabeculopuncture and Cyclodialysis, Ophthalmol. (1979) 179:189-200.

Van Gernert, et al., Clinical Use of Laser Tissue Interactions, IEEE Engineering in Medicine and Biology Magazine (1989) 10-13.

Venkatesh, et al., In Vitro Studies with a Pulsed Neodymium/YAG Laser, British J. of Ophth. (1985) 69:86-91.

Agarwal, et al., Textbook of Ophthalmology (2002) 2:1515.

Alm, et al., Uveoscleral Outflow—A Review, Exp. Eye Res. (2009) 88:760-768.

Gaasterland, et al., Long-Term Effects of Q-Switched Ruby Laser on Monkey Anterior Chamber Angle, Invest. Ophth. & Vis. Sci. (1985) 26(2):129-135.

Garg, Innovative Techniques in Ophthalmology (2006) 257.

Goldschmidt, et al., Theoretical Approach to Laser Trabeculotomy, Med. Phys. (1978) 5(2):92-99.

Ham, et al., Physiological Effects of Laser Trabeculotomy in Rhesus Monkey Eyes, Invest. Ophtalmol. Visual Sci. (1977) 16(7):624-628.

Hill, et al., Ab-Interno Erbium (Er): YAG Laser Sclerostomy With Iridotomy in Dutch Cross Rabbits, Lasers Surg. & Med. 13:559-564 (1993).

Hill, et al., Effects of Pulse Width on Erbium: YAG Laser Photothermal Trabecular Ablation (LTA), Lasers Surg. & Med. (1993) 13:440-446.

Hill, et al., Laser Trabecular Ablation (LTA), Lasers Surg. & Med. (1991) 11:341-346.

Kahook, Iridoplasty: Advice on Appropriate Technique, Glaucoma Today (Jul./Aug. 2006).

Krug, et al., The Glaucoma Laser Trial (GLT) and Glaucoma Laser Trial Follow-up Study 7 Results, Amer. J. Ophthamol. (1995) 120(6):718-731.

\* cited by examiner

Conventional Outflow Pathway - TM

Non-Conventional Outflow Pathway - Uveoscleral

Angle-Closure Glaucoma

Primary Open-Angle Glaucoma,
Pigmentary Glaucoma, and Exfoliation Glaucoma

Laser Iridoplasty

Partial Iris Spot

Full Iris Spot
-w-
Pupillary Beam Blank or Occlusion

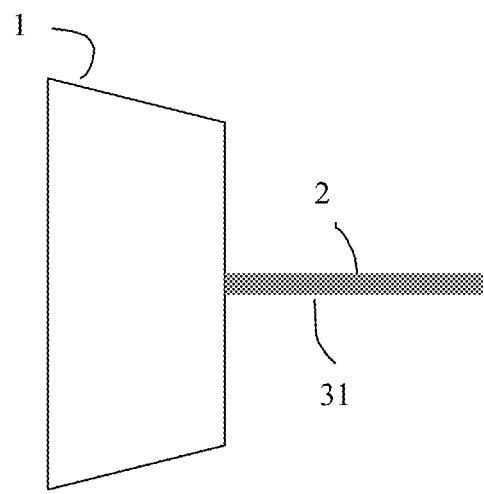
FIG. 25
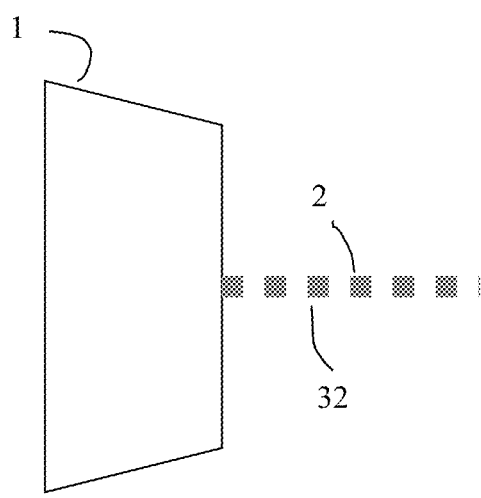 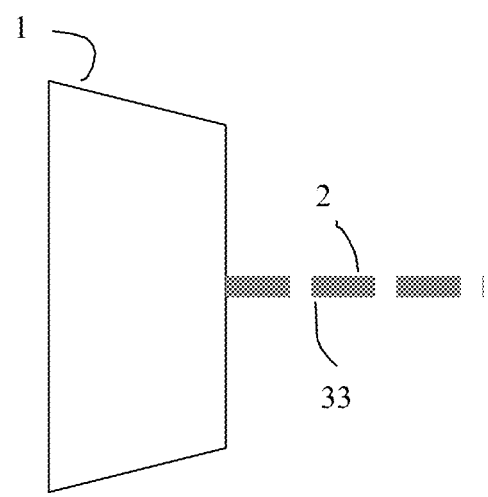
FIG. 26                FIG. 27

METHOD FOR LASER TREATMENT FOR GLAUCOMA

BACKGROUND OF THE INVENTION

Glaucoma is a family of optic neuropathies which cause irreversible but potentially preventable vision loss. Vision loss in most forms of glaucoma is related to elevated intraocular pressure or "IOP" with subsequent injury to the optic nerve. Secretion of aqueous humor and regulation of its outflow are physiologically important processes for maintaining IOP in the normal range. See FIGS. 1-2.

Treatment protocols for glaucoma currently include medication, conventional surgery, and laser surgery. Each of these protocols has significant side effects, complications, and limited long-term efficacy. Side effects of medication adverse interaction with other oral medications (such as aspirin, oral beta-blockers, calcium-channel blockers, and quinidine), aggravation of asthma and other lung-disease symptoms, allergic conjunctivitis, allergic reactions, altered taste, anemia, anterior uveitis, anxiety, brow-aches, burning, cataract, ciliary spasm, conjunctival thickening, convulsions, coronary arrhythmia, crib death in infants, depression, dim vision, dry mouth, enlarged pupils, epithelial keratopathy, eye pain, fatigue, follicular conjunctivitis, frequent urination, headaches, high blood pressure, increased heart rate, increased pupillary block, IOP reduction in fellow eyes, IOP spikes (especially when switching from other glaucoma medications), iris cysts, kidney problems, lethargy, lid elevation, loss of appetite, low blood pressure, macular edema in aphakic eyes, miosis, muscle and joint pain, muscular paralysis, nearsightedness, periocular contact dermatitis, pseudomyopia, reactivation of herpes keratitis, red and itching eyes and lids, reduction in corneal sensitivity, respiratory failure, retinal detachment, sexual dysfunction, stinging, stomach problems, tearing, weight loss, conjunctival hyperemia. See European Glaucoma Society, Terminology and Guidelines for Glaucoma 127-37 (3d ed. 2008); University of Illinois Eye & Ear Infirmary, The Eye Digest, Drug Treatment for Glaucoma (2003); New York Times, Health Guide, Glaucoma, In-Depth Report: Medications (Jun. 23, 2009) (hereinafter "NYT: Medications"), avail. Mar. 10, 2012, at <http://health.nytimes.com/health/guides/disease/glaucoma/medications.html>. In addition, adherence to medication protocols can be confusing and expensive. If side effects occur, the patient must be willing either to tolerate these or communicate with the treating physician to improve the drug regimen. Poor compliance with medication protocols and follow-up visits is a major reason for vision loss in glaucoma patients. See Health Guide: A New Understanding of Glaucoma, New York Times (Jul. 15, 2009), avail. on Mar. 10, 2012, at <http://www.nytimes.com/ref/health/healthguide/esn-glaucoma-ess.html>.

Examples of conventional surgical protocols include trabeculectomy, non-penetrating deep sclerectomy or "NPDS," canaloplasty, and glaucoma drainage implants. Complications include blister-like bumps or "blebs," scarring, cataracts, hypotony (very low eye pressure), detached retina, breakdown of the cornea, bleeding, and eye movement disorders, such as strabismus (crossed eyes) or diplopia (double-vision). See Kent, Which Glaucoma Surgery For Which Patient?, Rev. Ophthalmol. (Jun. 11, 2010), avail. on Mar. 10, 2010, at <http://www.revophth.com/content/d/cover_focus/c/22695/>; New York Times, Health Guide, Glaucoma, In-Depth Report: Surgery (Jun. 23, 2009) (hereinafter "NYT: Surgery"), avail. on Mar. 10, 2012, at http://health.nytimes.com/health/guides/disease/glaucoma/surgery.html; Detry-Morel, et al., Comparative Safety Profile Between "Modern" Trabeculectomy and Non-Penetrating Deep Sclerectomy, 300 Bull. Soc. Belge. Ophtalmol. 43-54 (2006), abstract avail. on Mar. 10, 2012, at http://www.ncbi.nlm.nih.gov/pubmed/16903511.

Laser surgical protocols may present fewer complications than conventional surgical protocols, but they may also provide lower long-term efficacy. These protocols include laser trabeculoplasty, peripheral iridotomy, trans-scleral diode laser cycloablation or "TDC," and laser-assisted NPDS. There are two types of laser trabeculoplasty: argon laser trabeculoplasty or "ALT" and selective laser trabeculoplasty or "SLT." Complications from both types of laser trabeculoplasty include post-surgical IOP increases, leading in some cases to vision loss, and development of adhesive-like substances called "peripheral anterior synechiae" that cause the iris to stick to part of the cornea. In addition, the effect of both forms of laser trabeculoplasty diminishes over time. In a retrospective analysis of longer term outcomes of SLT (n=41) compared to ALT (n=154), success was defined as an IOP decrease of at least 3 mmHg without additional medication or surgery. Success rate in the SLT group at 1, 3, and 5 year follow-up time points was 68%, 46%, and 32%, respectively, while in the ALT group it was 54%, 30%, and 31%. See Juzych, et al., Comparison of Long-Term Outcomes of Selective Laser Trabeculoplasty Versus Argon Laser Trabeculoplasty in Open Angle Glaucoma, 111 Ophthalmol. 1853-59 (2004).

The most commonly reported complications from LPI include conjunctivitis, corneal abrasion, pain, bleeding, inflammation, increased IOP, failure of the iridotomy to improve the drainage angle configuration, delayed closure of the iridotomy, and corneal scarring. Gray, et al., Efficacy of Nd-YAG Laser Iridotomies in Acute Angle Closure Glaucoma, 73 Br. J. Ophthalmol. 182-85 (1989). Additional complications include aqueous misdirection, corneal decompensation, cataract development, retinal damage, and photopsias or ghost images. See Mayer, Keeping Glaucoma Laser Therapy on Target: Strategies for Avoiding and Managing the Complications Involved in Three Common Glaucoma Laser Procedures (October 2011).

TDC complications include post-surgical IOP spikes, loss of visual acuity (two lines or more), corneal decompensation, phthisis bulbi, and corneal graft rejection. See Yap-Veloso, et al., Intraocular Pressure Control After Contact Transscleral Diode Cyclophotocoagulation in Eyes with Intractable Glaucoma, 7 J. Glaucoma 319-28 (1998).

Complications from laser-assisted NPDS include choroidal detachment, corneal edema, bleb encapsulation, postoperative hyphema, shallow anterior chamber, anterior chamber inflammation, hypotonia, choroidal detachments, increased resistance to aqueous outflow through Descemet's membrane. See Klink, et al., Erbium-YAG Laser-Assisted Preparation of Deep Sclerectomy, 238 Graefe's Arch. Clin. Exp. Ophthalmol. 792-96 (2000).

A need exist for a glaucoma treatment protocol with good long-term efficacy and fewer side effects and complications

BRIEF SUMMARY OF THE INVENTION

Because vision loss in most forms of glaucoma is related to elevated IOP, most glaucoma treatment protocols are concerned with lowering IOP by increasing aqueous humor outflow. In healthy eyes, equilibrium exists between the production and drainage of aqueous humor. See FIGS. 1-2. Disruption of aqueous outflow results in elevation of IOP.

Aqueous outflow occurs via two pathways, a conventional pathway and a non-conventional pathway, both of which are located at the at anterior chamber drainage angle. The conventional pathway is the trabecular meshwork or "TM" pathway. See FIG. 1.

The primary causes of aqueous outflow restriction include narrowing of the drainage angle formed where the cornea and the iris meet (due to an increase in lens size with age or an increase in iris convexity) (see FIG. 3), abrasion of posterior iris pigment and discharge into the aqueous humor and onto the TM (resulting in part from a decrease in iris convexity and thus an increase in proximity between the zonule fibers of the ciliary body and the posterior iris epithelium) (see FIG. 4), and the exfoliation of ocular debris its buildup in the TM (see FIG. 4). In many cases, IOP would be relieved by a reduction in iris convexity or concavity or an increase in lateral tension on the TM or uveoscleral pathways.

The invention utilizes electromagnetic radiation to create retraction in the iris tissue, thereby (a) reducing convexity and enlarging the drainage angle and thus the area of the anterior chamber, (b) reducing contact between the zonule fibers and the iris pigment epithelium, (c) applying greater tension to both the TM and uveoscleral outflow pathways, thereby enlarging those pathways and increasing outflow.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 10 shows an anterior surface (3) of an iris (4) to which no laser radiation has been applied. FIG. 11A shows an anterior surface (3) of an iris (4) to which laser radiation has been applied to approximately (but less than) the entire anterior surface (3) by reason of the spared tissue between laser spots. FIG. 11B shows a magnified partial view of FIG. 11A, i.e., an anterior surface (3) to which laser radiation has been applied to approximately (but less than) an entire anterior surface (3) by reason of the spared tissue (7) between laser spots (8). FIG. 12 shows an anterior surface (3) of an iris (4) to which laser radiation has been applied to approximately (but less than) an entire anterior surface (3) by reason of the untreated peripheral iris (9). FIG. 13 shows an anterior surface (3) of an iris (4) to which laser radiation has been applied to approximately (but less than) an entire anterior surface (3) by reason of the untreated pupillary zone (10).

FIG. 14A shows an iris (4), the retraction in at least a portion of which has not been induced by the application of laser radiation to its anterior surface (3). FIG. 14B shows an iris (4), the retraction in at least a portion of which has been induced by the application of laser radiation to its anterior surface (3). Retraction is symbolized in FIGS. 14A and 14B by the expansion of space between the horizontal and vertical lines from FIG. 14A to FIG. 14B.

FIG. 15A shows an iris (4), the retraction in at least a portion of which has not induced a reduction in its convexity (11). FIG. 15B shows an iris (4), the retraction in at least a portion of which has induced a reduction in its convexity (11).

FIG. 16A shows an iris (4), the retraction in at least a portion of which has not induced an enlargement of the drainage angle (12). FIG. 15B shows an iris (4), the retraction in at least a portion of which has induced an enlargement of the drainage angle (12).

In FIG. 22A, the computer guided tracking system (20) detects movement (21) of the eye (5) along the x-y plane and adjusts (22) the position of the laser beam (2) to follow the movement (21). In FIG. 22B, the computer guided tracking system (20) detects movement (23) of the eye (5) along the z axis and adjusts (24) the position of the laser beam (2) to follow the movement (23).

FIG. 25 shows aspects of an embodiment of the invention, which aspects comprise a laser (1) and a laser beam (2), wherein the laser (1) generates laser radiation (2) in the infrared spectrum (31).

FIGS. 26 and 27 show aspects of an embodiment of the invention, which aspects comprise a laser (1) and a laser beam (2). In FIG. 26, the laser (1) generates a laser beam (2) with a pulse width in the nanosecond range (32). In FIG. 27, the laser (1) generates a laser beam (2) with a pulse width in the microsecond range (33). The length of the dashes in each beam symbolizes the duration of its pulse width.

DETAILED DESCRIPTION OF THE INVENTION

Figure 1:
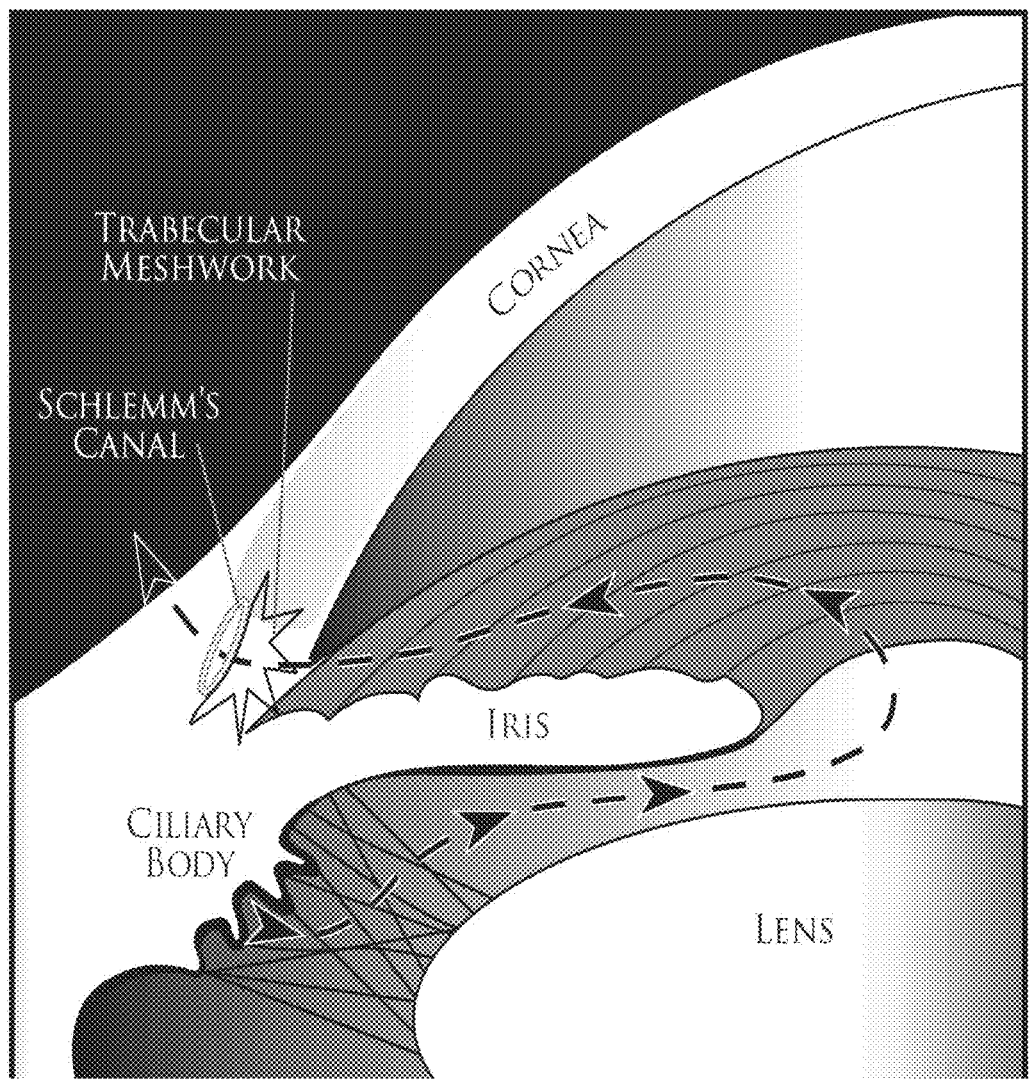
FIG. 1 shows the aqueous humor moving through the conventional (TM) outflow pathway.
Figure 2:
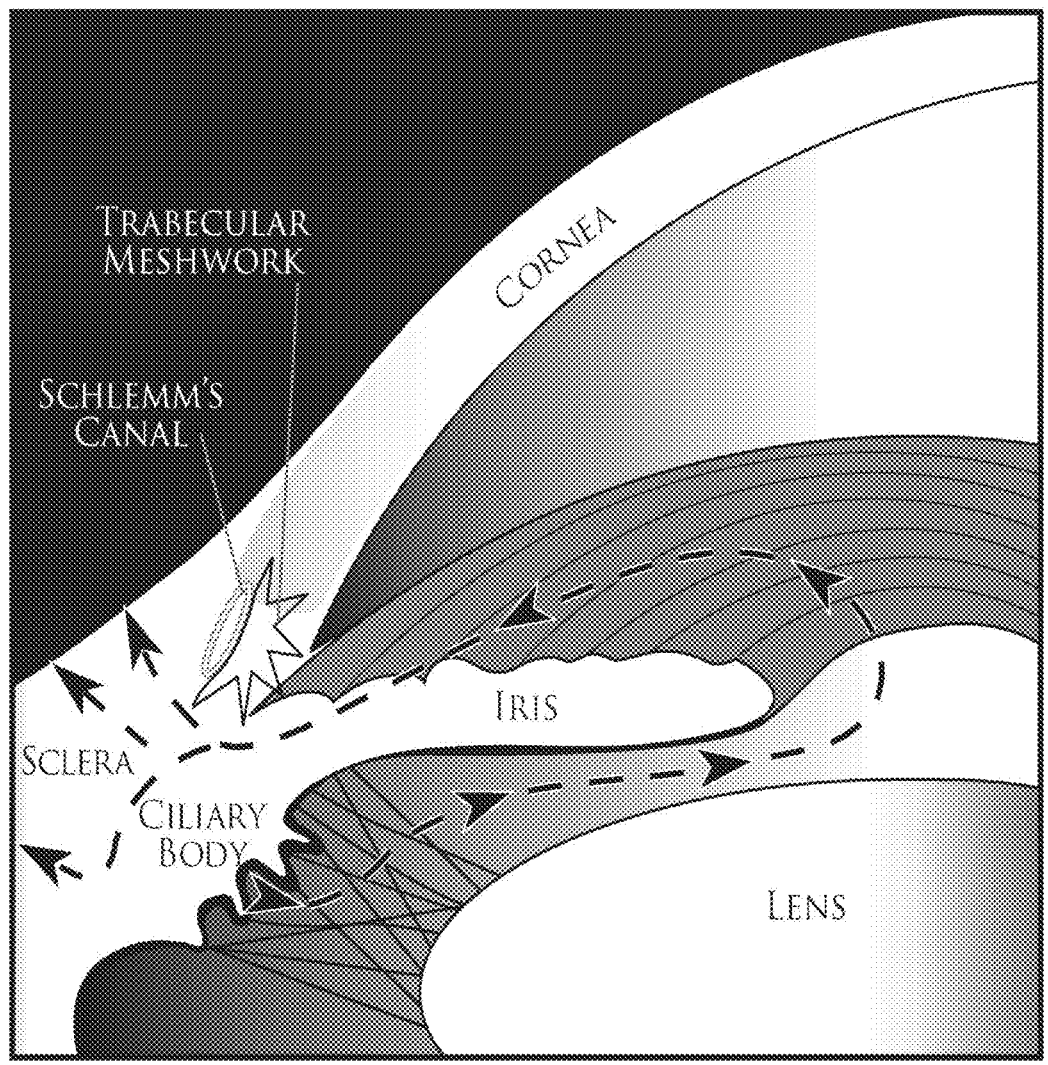
FIG. 2 shows the aqueous humor moving through the non-conventional (uveoscleral) outflow pathway.

Because vision loss in most forms of glaucoma is related to an elevation in IOP, most glaucoma treatment protocols are concerned with lowering IOP by increasing aqueous humor outflow. In healthy eyes, equilibrium exists between the production and drainage of aqueous humor. See FIGS. 1-2. Disruption of aqueous outflow results in elevation of IOP.

Aqueous outflow occurs via two pathways, a conventional pathway and a non-conventional pathway, both of which are located at the at anterior chamber drainage angle, where the cornea and the iris meet. The conventional pathway is the trabecular meshwork or "TM" pathway. See FIG. 1. The aqueous humor passes through the TM, across the inner wall of Schlemm's canal, into its lumen, and into draining collector channels, aqueous veins, and episcleral veins. The non-conventional pathway is the uveoscleral pathway. See FIG. 2. It is composed of the uveal meshwork ("UM") and the anterior face of the ciliary muscle. The aqueous humor enters the connective tissue between the muscle bundles, through the suprachoroidal space, and out through the sclera. Most commentators contend that resistance to the aqueous humor outflow is localized primarily to the TM, so IOP-lowering therapies tend to focus on the TM pathway. Considerable data suggest, however, that 40-50% of aqueous humor exits the eye by the uveoscleral pathway, and this percentage tends to rise with age. See generally Alm, et al., Uveoscleral Outflow—A Review, 88 Exp. Eye Res. 760-68 (2009).

Figure 3:
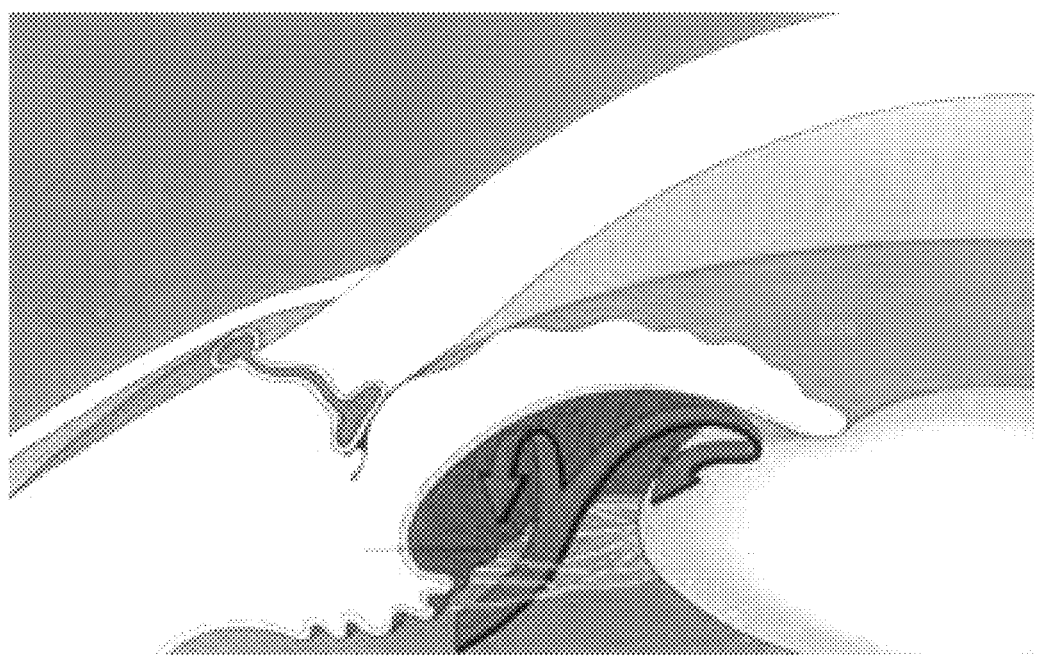
FIG. 3 shows angle-closure glaucoma.
Figure 4:
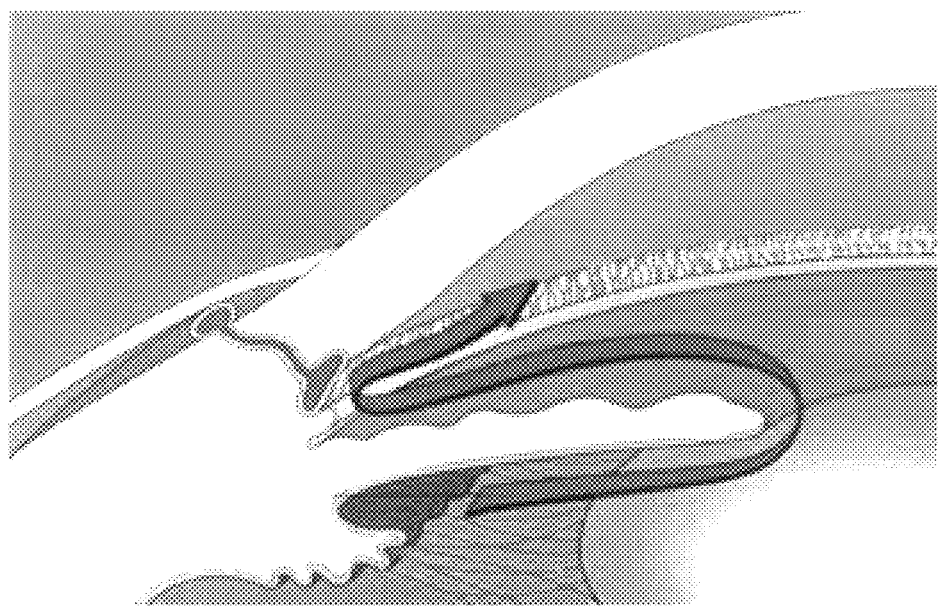
FIG. 4 shows primary open-angle glaucoma, pigmentary glaucoma, and exfoliation glaucoma.
Figure 5:
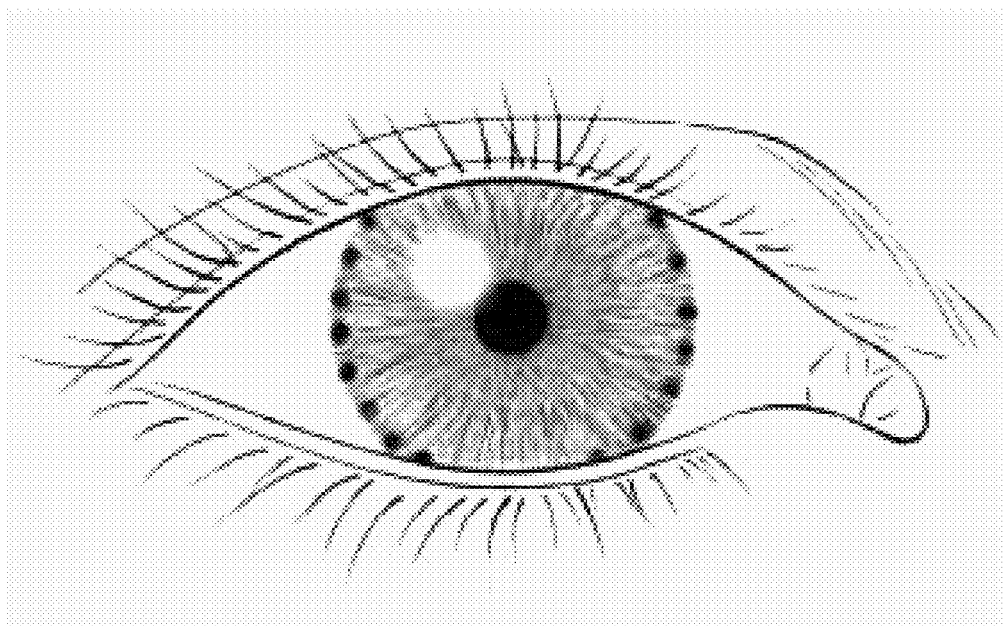
FIG. 5 shows the treatment area of the laser iridoplasty.
Figure 6:
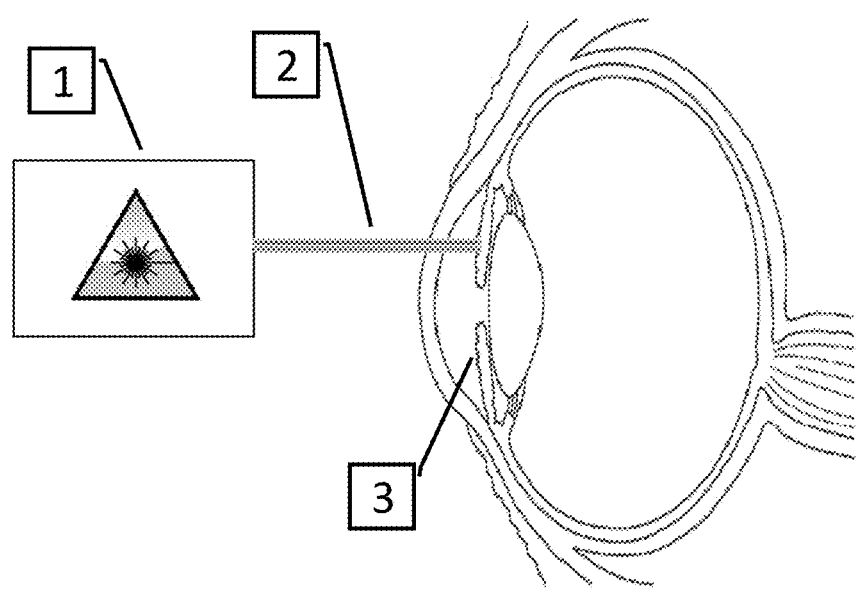
FIG. 6 shows aspects of an embodiment of the invention wherein an EMR device (1) delivers a beam (2) to the anterior surface of the iris of the patient (3), and the spot on the iris is smaller than the diameter of the iris.

Restriction of aqueous outflow may occur in either the anterior chamber or the posterior chamber of the eye. Outflow restriction in the anterior chamber occurs when outflow is limited at the drainage angle. This can result from a narrowing of the drainage angle due to an increase in lens size with age or an increase in iris convexity (see FIG. 3), abrasion of posterior iris pigment and discharge into the aqueous humor and onto the TM (resulting in part from a decrease in iris convexity and thus an increase in proximity between the zonule fibers of the ciliary body and the posterior iris epithelium) (see FIGS. 5-6 FIG. 4), and the exfoliation of ocular debris its buildup in the TM (see FIG. 4). In these cases, IOP can be relieved by a reduction in iris convexity or concavity or an increase in lateral tension on the TM or uveoscleral pathways, thereby expanding these pathways, increasing outflow, and relieving IOP.

Outflow restriction in the posterior chamber may occur when the area between the pupil and the anterior capsule of the lens is narrowed, restricting aqueous flow from the posterior chamber into the anterior chamber and causing IOP to build up behind the iris. This condition is called "pupillary block." In these cases, IOP can be relieved by an iridotomy or iridectomy, whereby a hole is created in the iris, connecting the posterior and anterior chambers and reducing IOP in the posterior chamber. IOP can also be relieved by an increase in lateral tension on the pupil thereby increasing the area between the pupil and the anterior lens capsule and reducing IOP in the posterior chamber.

The present invention utilizes electromagnetic radiation ("EMR") to create retraction or shrinkage in the iris tissue, thereby (a) reducing iris convexity and enlarging the drainage angle to improve aqueous outflow through both the TM and uveoscleral outflow pathways, (b) reducing iris concavity, thereby limiting contact between the zonule fibers and the iris pigment epithelium and reducing abrasion of the iris pigment epithelium and the dislodgement of posterior iris pigment that might clog the TM and reduce outflow, (c) applying greater tension to both the TM and uveoscleral outflow pathways, thereby enlarging those pathways and increasing outflow, and (d) increasing lateral tension on the pupil, thereby increasing the area between the pupil and the anterior lens capsule and reducing IOP in the posterior chamber. Iris retraction or shrinkage is achieved by applying EMR to the anterior iris.

The use of laser energy to shrink iris tissue is well-known in the art, and other glaucoma therapies rely on iris tissue retraction to relieve IOP. See, e.g., Garg, Innovative Techniques in Ophthalmology 257 (2006); Agarwal, et al., 2 Textbook of Ophthalmology 1515 (2002); Ritch, et al., Argon Laser Peripheral Iridoplasty, 27 Ophthalmol. Surg. & Lasers 289 (1996). During a laser iridoplasty, laser energy is applied in spots (generally 100-500µ in diameter) along the peripheral iris to achieve contraction of the iris tissue. See FIG. 5. When the peripheral iris shrinks, it places tension on the TM and enlarges the drainage angle. See Kahook, Iridoplasty: Advice on Appropriate Technique, Glaucoma Today (July/August 2006). The mechanisms of action of iris tissue shrinkage is thought to be (a) an immediate thermal response, whereby the laser energy is converted to heat that causes contraction of stromal collagen, and (b) a later proliferation of fibroblasts and the formation of a contraction membrane. See id. Another glaucoma treatment that may rely on a laser tissue-shrinkage response is the laser trabeculoplasty (ALT and SLT) described above. In that case, however, (i) it is unclear whether tissue shrinkage, pigment removal, or both are responsible for the increase in aqueous outflow, and (ii) the laser is applied solely to the TM, which is generally not considered to be part of the iris as it differs from the iris in both location and composition.

The present invention, by contrast, treats other areas of the anterior iris (which may or may not include the peripheral iris, the TM, and/or the UM). The advantages of treating these other areas include one or more of the following: (a) greater iris tissue retraction is achieved, placing more tension on the TM and uveoscleral outflow pathways and the pupil and producing greater outflow and a greater reduction in IOP, (b) faster iris tissue retraction is achieved, thereby reducing IOP more quickly (which in some cases can mean the difference between preservation of sign and loss of sight), and (c) longer-lasting iris tissue retraction, thereby increasing the time between retreatments or eliminating retreatment altogether.

As used in this disclosure, "EMR" includes any form of electromagnetic radiation, whether in the form of sound, heat, light, or otherwise, and whether consisting of radio frequency, ultrasound, microwave, infrared, visible light, ultraviolet, x-ray, t-ray, gamma ray, or otherwise. The term "EMR" is not intended to restrict the form of radiation in terms of monochromaticity (i.e., composed of one or more than one different wavelength), directionality (i.e., produce a single non-divergent spot or radiate in several different directions), or coherence (i.e., the waves produced consist of a single phase relation or of multiple phase relations). Moreover, the frequency of the EMR can be any frequency within the EMR spectrum, including, without limitation, extremely low frequency sound radiation (with a frequency of 3 Hz) to gamma radiation (with a frequency of 300 EHz). The EMR can be delivered in a continuous wave or in pulses, and the pulse width may be any time interval, including microseconds, nanoseconds, picoseconds, femtoseconds, or attoseconds. If pulsed, any repetition rate may be used, including, without limitation, repetition rates from 1 Hz to 100 THz. In addition, any energy output may be used, and any energy density may be created at the target treatment side, including, without limitation, energy outputs from 1 W to 1000 W. Finally, any gain medium may be used, including, without limitation, glass, solid, liquid, gas, crystal, or semiconductor. In the case of laser energy, the specific gain media may comprise Nd:YAG, alexandrite, pulsed-dye, or any other medium.

The term "beam" includes any EMR pathway, such as a laser beam, radio frequency pathway, ultrasound pathway, microwave pathway, infrared pathway, visible light pathway, ultraviolet pathway, x-ray pathway, t-ray pathway, gamma ray pathway, or otherwise. In addition, the beam may be fully collimated or any drainage angle of divergence or convergence. Finally, the term "beam" should be understood to include a single beam or multiple beams, and the multiple beams may result from the splitting or screening of a single beam or the generation of multiple beams with multiple frequencies, shapes, energy densities, and other characteristics. If the beam is a laser beam, it may or may not be fired through a goniolens.

The term "spot" includes the plane of intersection between the beam and the target cells or tissue, such as the laser spot, radio frequency site, ultrasound site, microwave site, infrared site, visible light site, ultraviolet site, x-ray site, t-ray site, gamma ray site, or otherwise. The term "EMR" is not intended to limit the beam or spot to any particular shape, size, or angle of projection. Spots can be tangent, overlapped, or isolated, and overlapping may occur in any direction (x, y, or z). They can also be square, rectangular, circular, elliptical, triangular, trapezoidal, torus, or otherwise. Finally, they can measure 1µ to 15 mm or otherwise.

Preferably, the energy density of the beam is set to a level that minimizes the damage to any ocular tissue while still providing satisfactory tissue retraction. Although the preferred EMR frequencies will pass through the cornea without causing any corneal injury, the method of the present invention can further include creating an opening in the cornea before applying the beam. Once the opening has been created, the beam may be introduced directly through the opening or via a beam-conducting vehicle, such as light-conducting fiber. If necessary, a temporary contact lens can be applied to reduce post-operative discomfort.

Additionally, the procedure may be repeated in order to further retract the iris tissue after allowing the iris and associated tissue to heal from the original application. For example, the method can be repeated from one day to two years after first applying the beam to the iris.

Movement of the beam may be guided by a computerized scanning system. Such systems are well-known in the art. See, e.g., Zyoptix Custom Wavefront LASIK (Bausch & Lomb, Rochester, N.Y.). The scanning system can be implemented using one or more computer systems. An exemplary computer system can include software, monitor, cabinet, keyboard, and mouse. The cabinet can house familiar computer components, such as a processor, memory, mass storage devices, and the like. Mass storage devices may include mass disk drives, floppy disks, Iomega ZIP™ disks, magnetic disks, fixed disks, hard disks, CD-ROMs, recordable CDs, DVDs, DVD-R, DVD-RW, Flash and other nonvolatile solid-state storage, tape storage, reader, and other similar media, and combinations of these. A binary, machine-executable version, of the software of the present invention may be stored or reside on mass storage devices. Furthermore, the source code of the software of the present invention may also be stored or reside on mass storage devices (e.g., magnetic disk, tape, or CD-ROM). Furthermore, a computer system can include subsystems such as central processor, system memory, input/output (I/O) controller, display adapter, serial or universal serial bus (USB) port, network interface, and speaker. The present invention may also be used with computer systems with additional or fewer subsystems. For example, a computer system could include more than one processor (i.e., a multiprocessor system) or a system may include a cache memory. The beam may be guided in any shape or pattern, including, without limitation, a spiral pattern, a raster pattern, or a segregated regional pattern.

Computer-guided tracking may be used to follow the eye in the x, y, or z directions (active tracking) or interrupt transmission (passive tracking) if the patient's head or eye moves during treatment. Computer-guided tracking systems are well-known in the art. See, e.g., SMI Surgery Guidance (SensoMotoric Instruments GmbH, Teltow, Germany).

In one embodiment of the invention, the iris is treated with a Q-switched, frequency-doubled Nd:YAG laser (532 nm). A topical anesthetic (lidocaine hydrochloride) is applied, as well as a miotic solution (pilocarpine) to ensure maximum exposure of the iris surface for treatment. The patient's irides are hazel; the darker stromal pigment serves as a favorable chromophore for the 532 nm wavelength. The laser produces a circular spot with a diameter of 250µ, and an energy density of 1.0 J/cm 2. The beam divergence is 17%. The pulse width is 20 ns. The laser is computer-guided in a spiral scan pattern across the entire iris. The spiral begins along the circumference of the pupil and spreads to the outer periphery of the iris. The spot separation is 125µ, (i.e., 50% overlap along x), and the line separation is 250µ, (i.e., 0% overlap along y). The patient's head is stabilized using the Mayfield Horseshoe Headrest (Integra LifeSciences Corporation, Plainsboro, N.J.), and the beam is fired in rapid succession while moving across the entire surface of the iris (repetition rate=5 kHz), with the angle of the beam either perpendicular to the iris surface or at any angle thereto. See FIG. 6. Movement of the beam is guided by a computerized scanning system. The scan is repeated 10 times. Computer-guided tracking is used to follow the eye in the x, y, or z directions (active tracking) and interrupt transmission (passive tracking) if the patient's head or eye moves during treatment.

Figure 7:
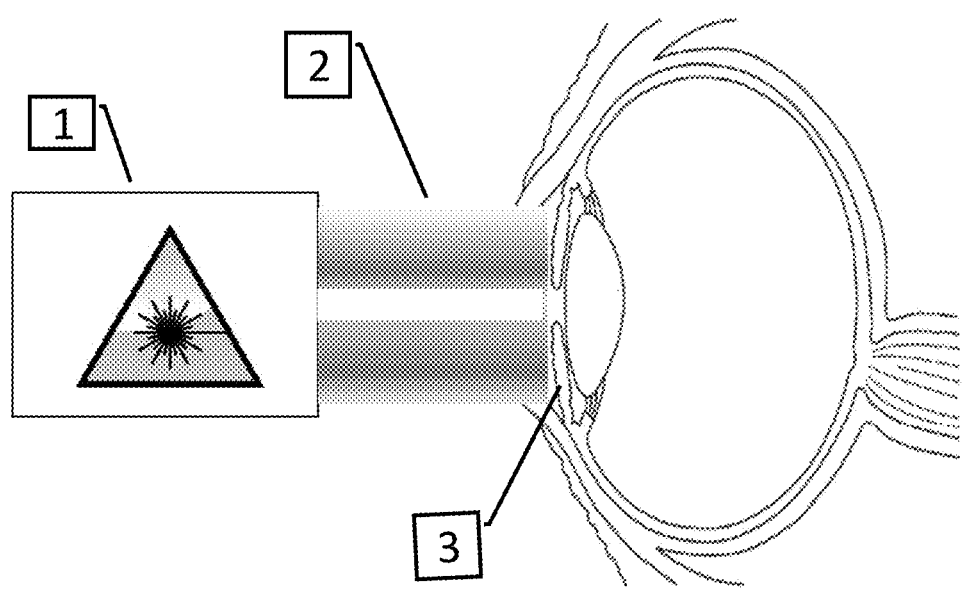
FIG. 7 shows aspects of an embodiment of the invention wherein an EMR device (1) delivers a beam (2) to the anterior surface of the iris of the patient (3), and the spot on the iris is approximately the same diameter as the iris (with the beam or energy path blanked or occluded at the pupil).
Figure 8:
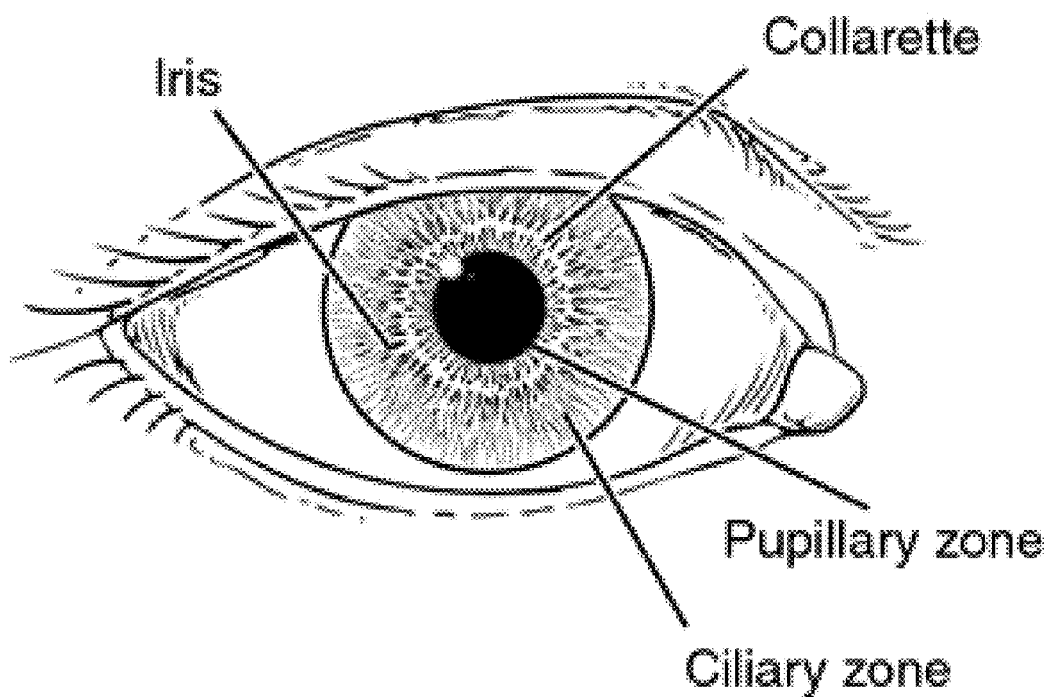
FIG. 8 shows the pupillary zone of the iris.
Figure 9:
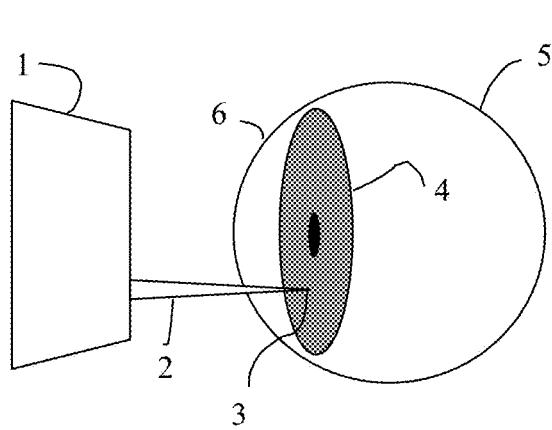
FIG. 9 shows aspects of an embodiment of the invention, which aspects comprise a laser (1), wherein the laser radiation (2) in the form of a beam is applied to the anterior surface (3) of an iris (4) of an eye (5), wherein stromal pigment resides on the anterior surface (3) of the iris (4), wherein a frequency of the laser radiation (3) is such that the laser beam is capable of passing through a cornea (6) of the eye (5), and wherein the frequency of the laser radiation (2) is such that the stromal pigment (3) serves as a chromophore for the laser beam (2).
Figure 10:
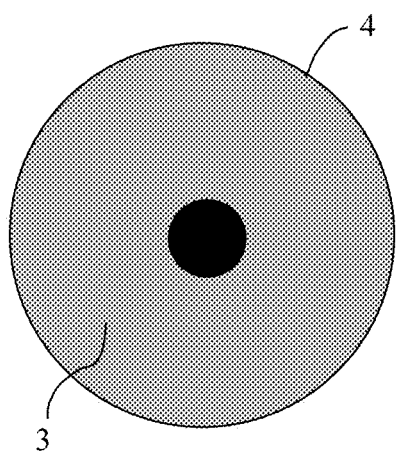
FIGS. 10, 11A, 11B, 12, and 13 show aspects of an embodiment of the invention, which aspects comprise an anterior surface (3) of an iris (4), wherein shading symbolizes the application of laser radiation, and non-shading symbolizes the non-application of laser radiation.
Figure 11A:
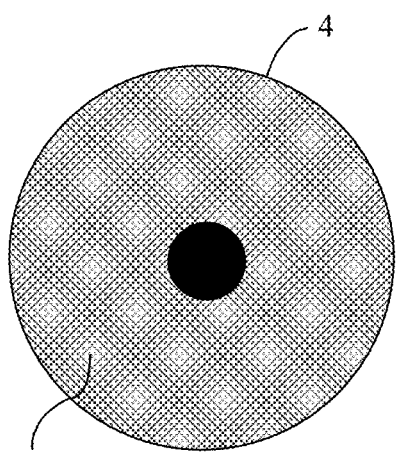
Figure 11B:
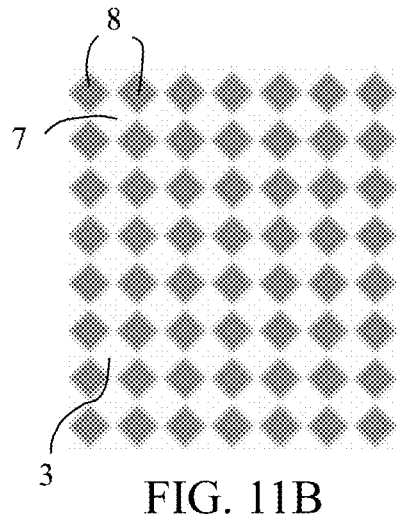
Figure 12:
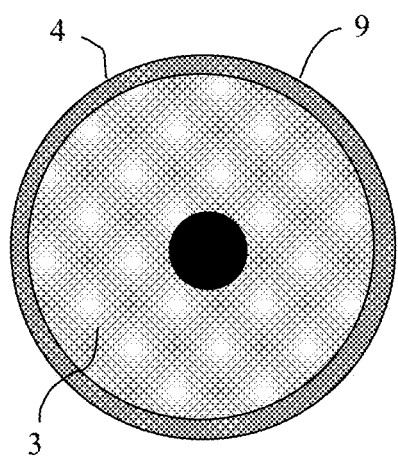
Figure 13:
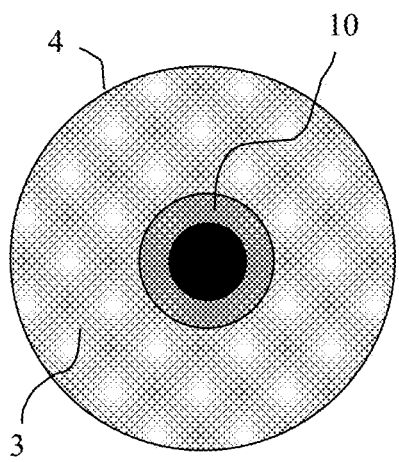
Figure 14A:
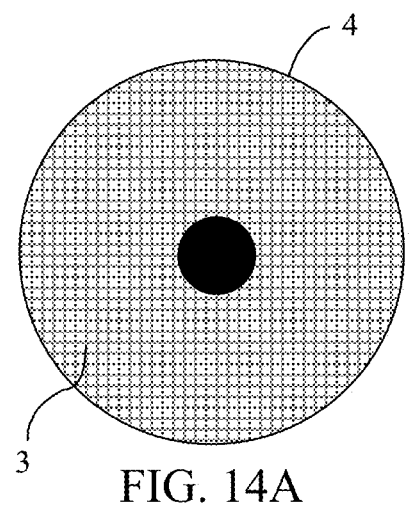
FIGS. 14A and 14B show aspects of an embodiment of the invention, which aspects comprise an iris (4) and its anterior surface (3).
Figure 14B:
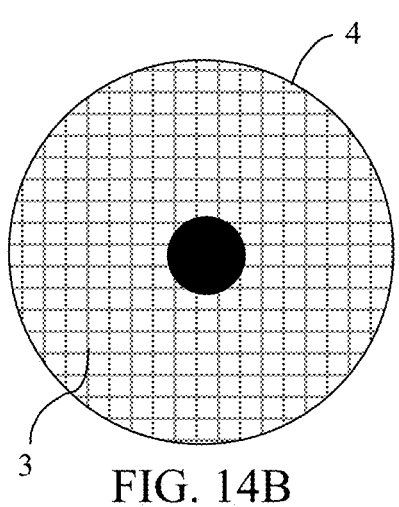
Figure 15A:
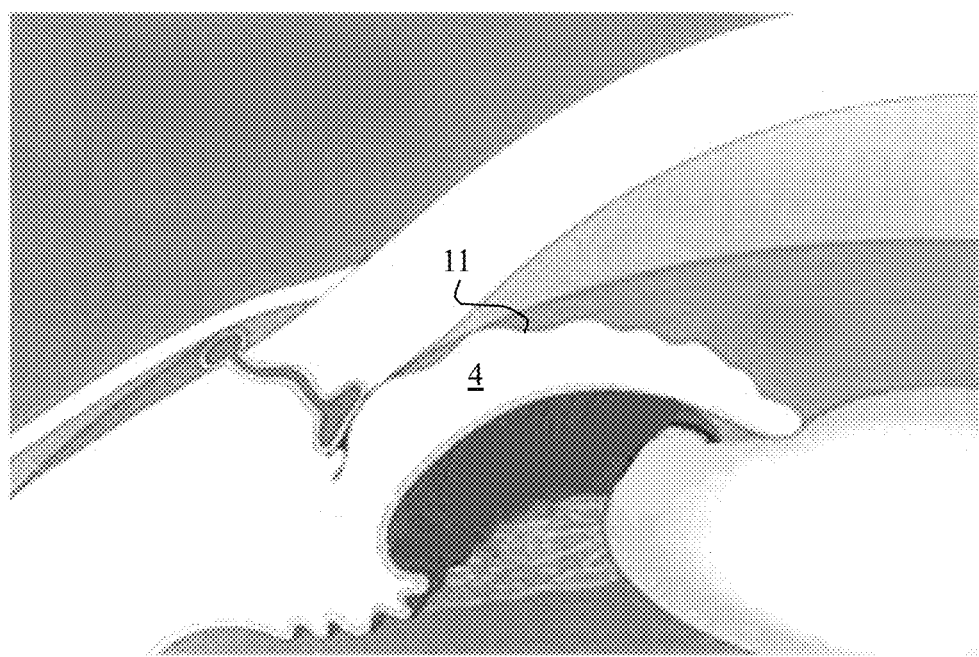
FIGS. 15A and 15B show aspects of an embodiment of the invention, which aspects comprise an iris (4).
Figure 15B:
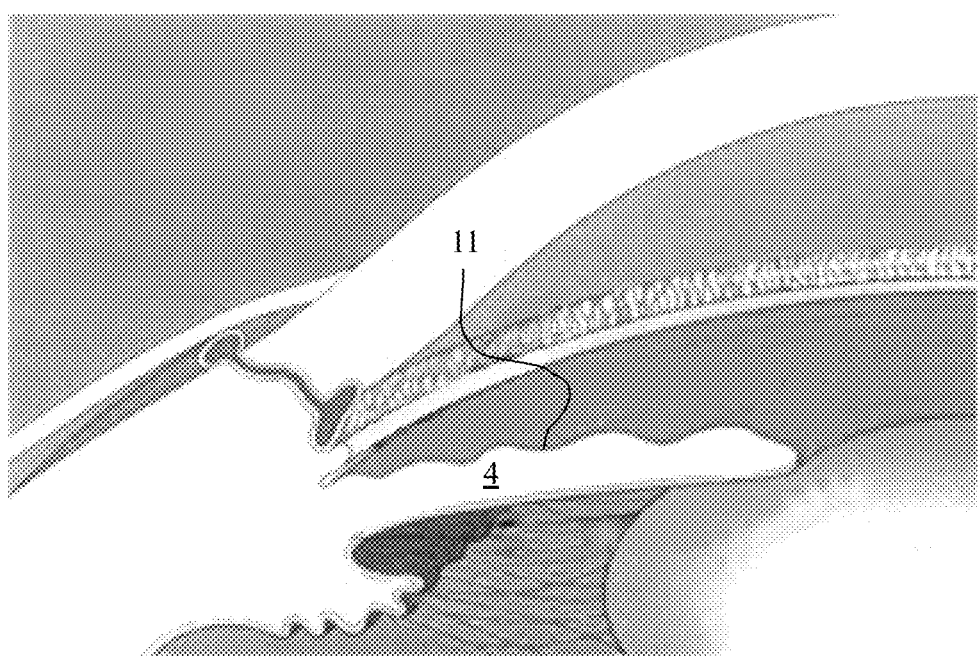
Figure 16A:
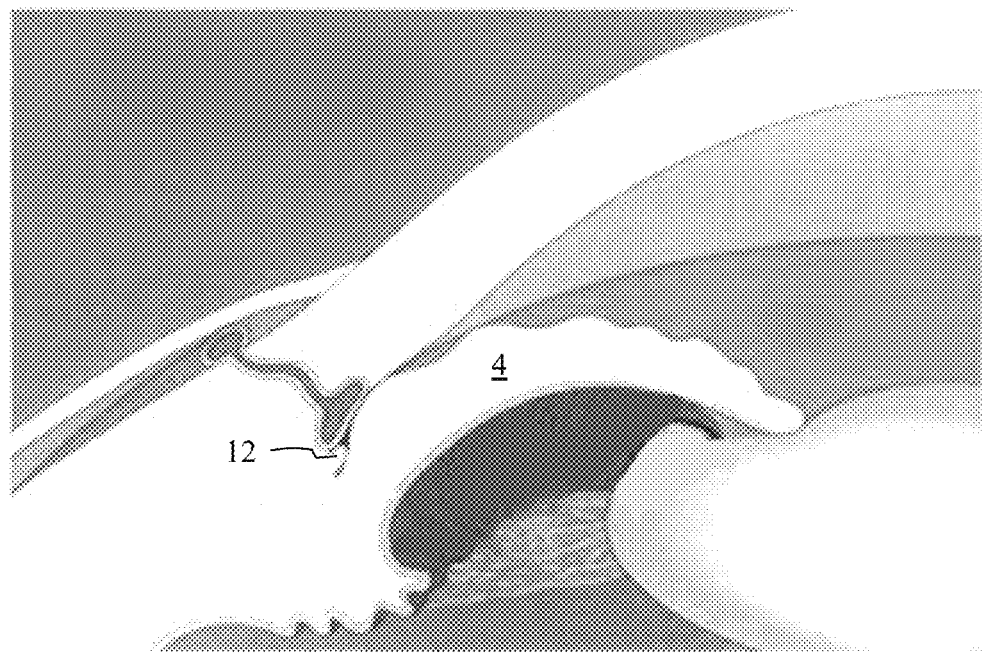
FIGS. 16A and 16B show aspects of an embodiment of the invention, which aspects comprise an iris (4) and a drainage angle (12) of an eye.
Figure 16B:
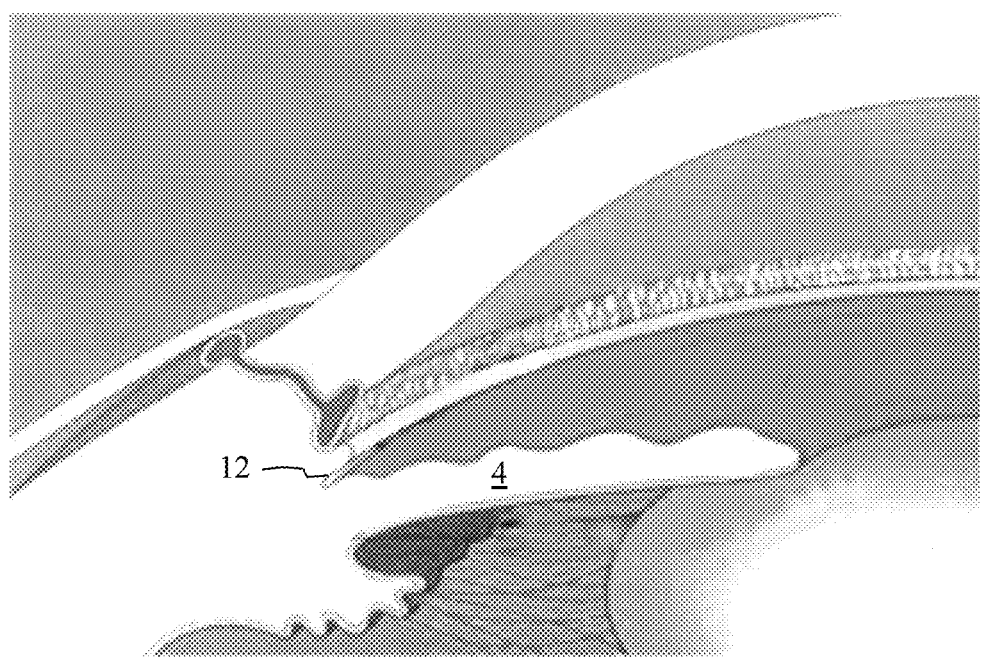
Figure 17:
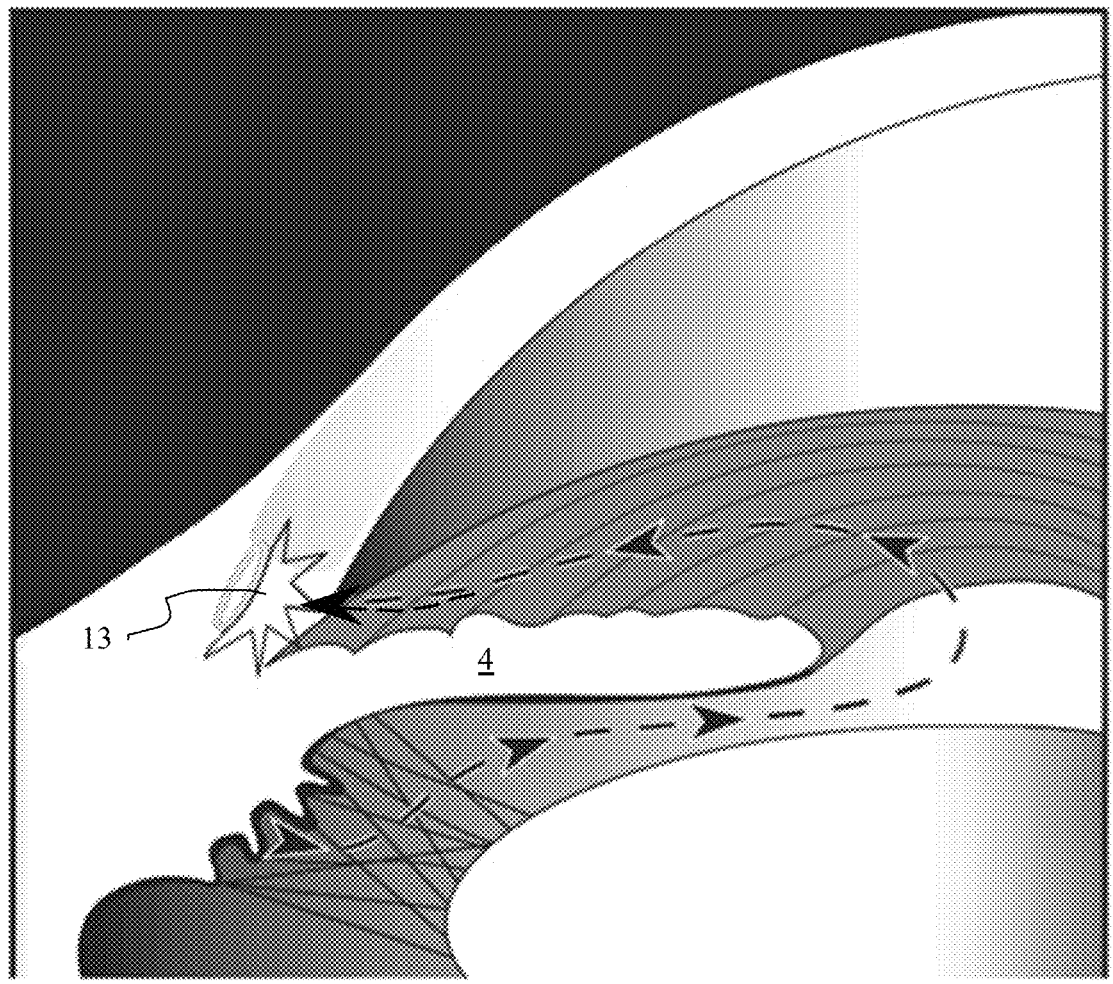
FIG. 17 shows aspects of an embodiment of the invention, which aspects comprise an iris (4) and a trabecular meshwork (13) of an eye, wherein the retraction in at least a portion of the iris (4) has induced an increase in aqueous outflow through the trabecular meshwork (13).
Figure 18:
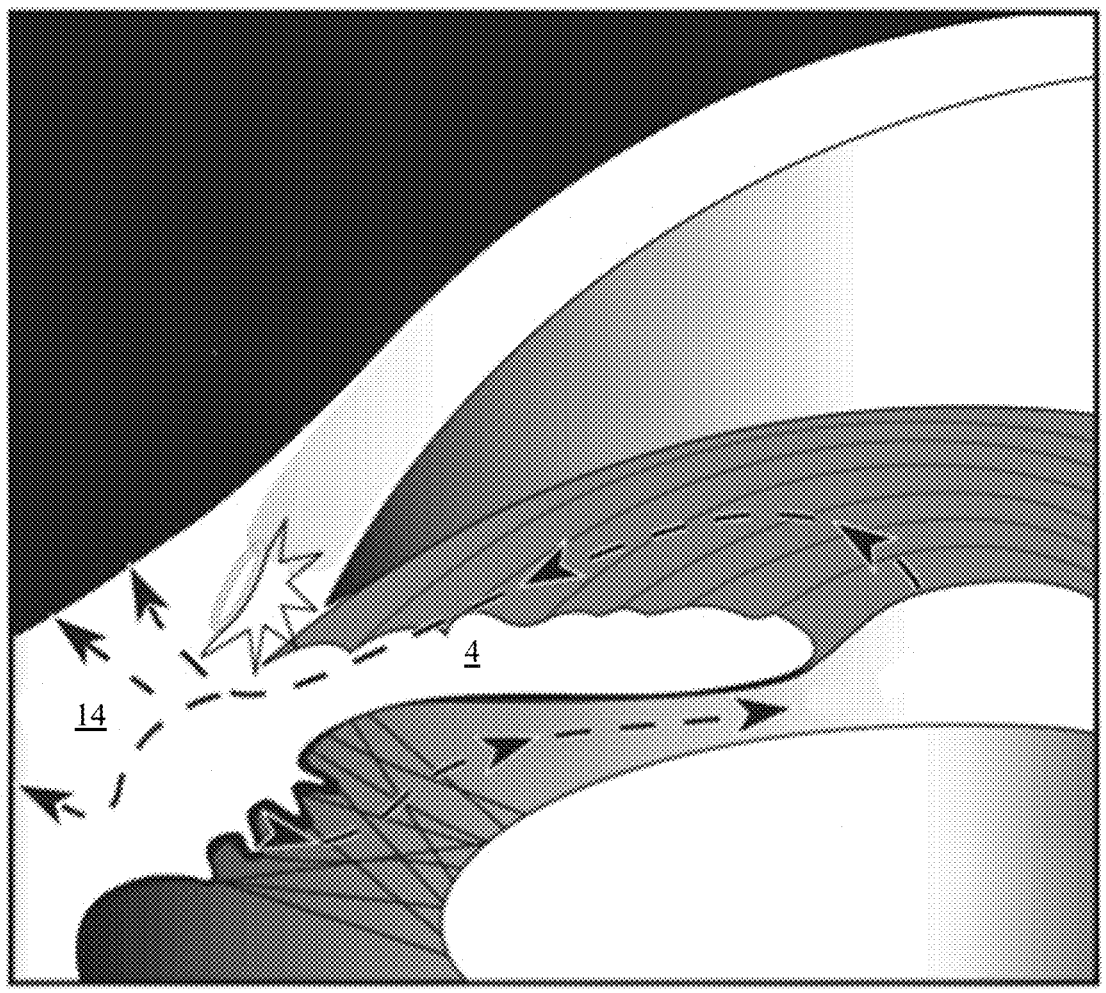
FIG. 18 shows aspects of an embodiment of the invention, which aspects comprise an iris (4) and a uveoscleral pathway (14) of an eye, wherein the retraction in at least a portion of the iris (4) has induced an increase in aqueous outflow through the uveoscleral pathway (14).
Figure 19:
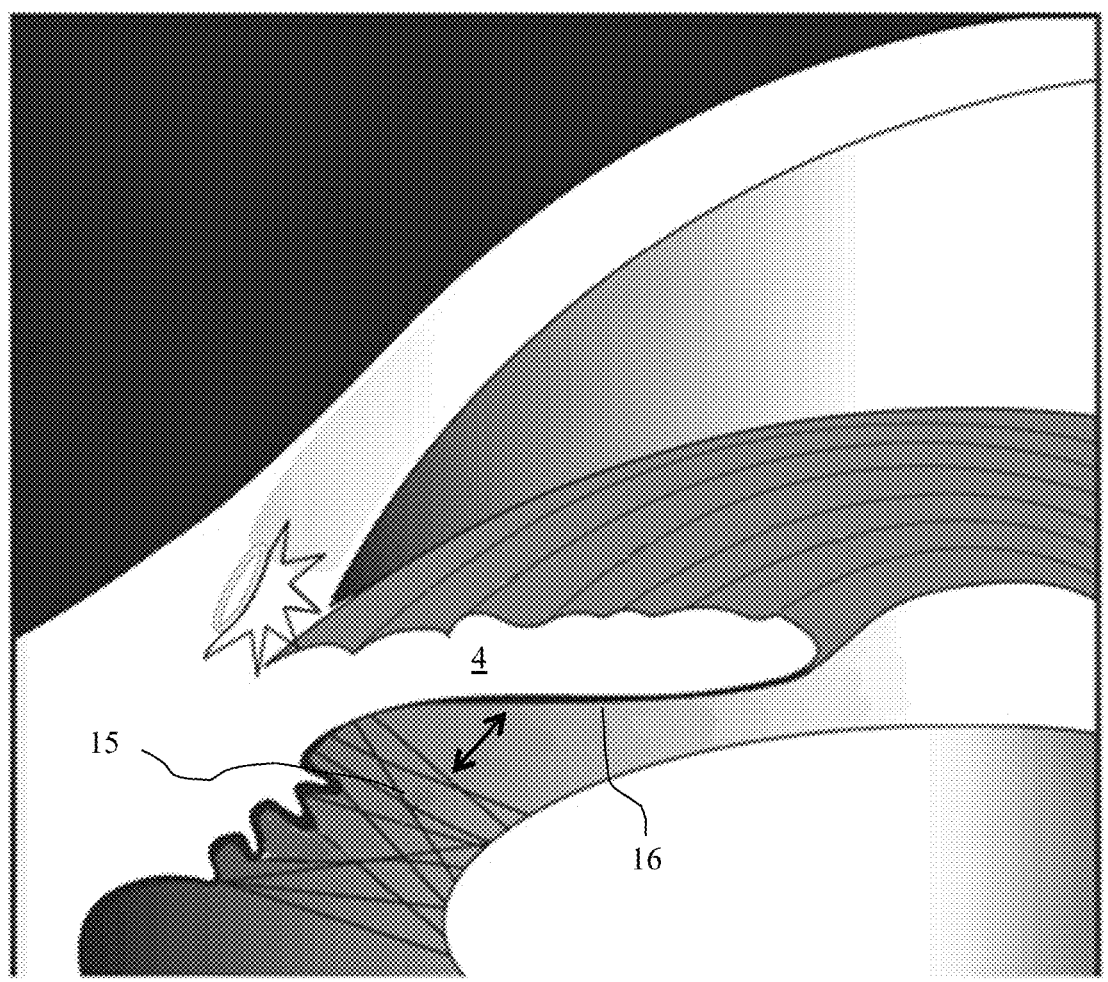
FIG. 19 shows aspects of an embodiment of the invention, which aspects comprise an iris (4), zonule fibers (15), and an iris pigment epithelium (16) of an eye, wherein the retraction in at least a portion of the iris (4) has induced a reduction in contact between the zonule fibers (15) and the iris pigment epithelium (16).
Figure 20:
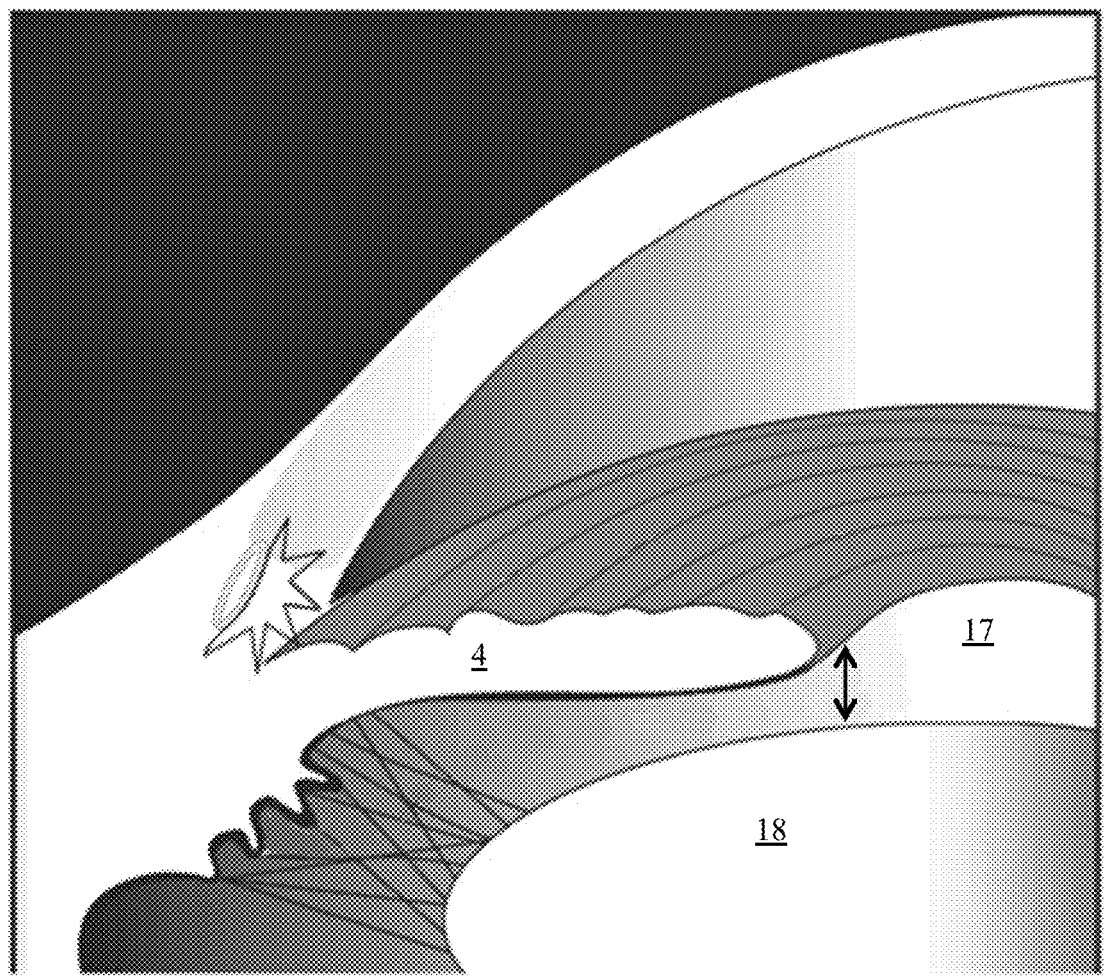
FIG. 20 shows aspects of an embodiment of the invention, which aspects comprise an iris (4), a pupil (17), and an anterior lens capsule (18) of an eye, wherein the retraction in at least a portion of the iris (4) has induced an increase in the area between the pupil (17) and the anterior lens capsule (18).
Figure 21:
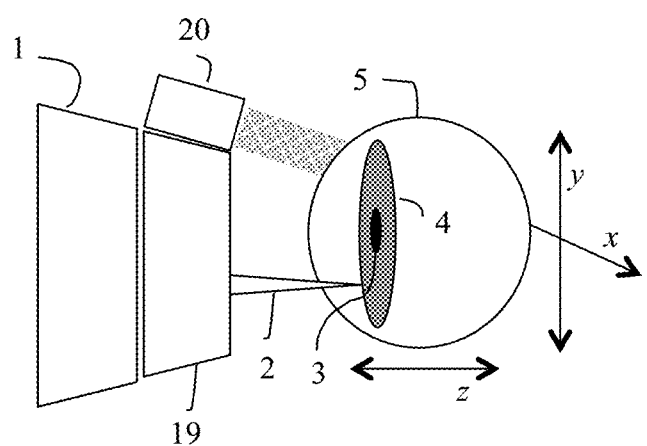
FIG. 21 shows aspects of an embodiment of the invention, which aspects comprise a laser (1), a computerized scanning system (19) configured to scan a laser beam (2) throughout the at least approximately entire anterior surface (3) of an iris (4), and a computer guided tracking system (20), configured to detect movement of the eye (5) in at least one of the x, y, and z directions.
Figure 22A:
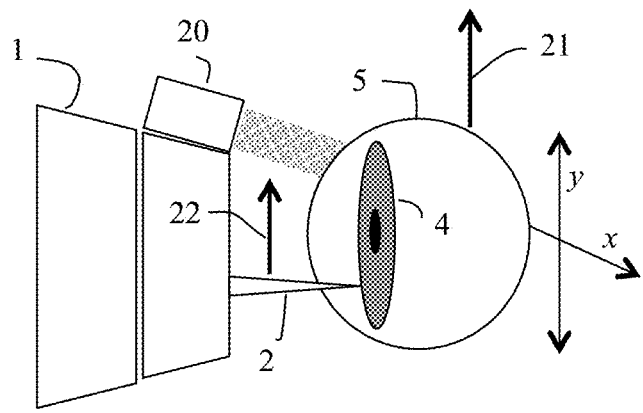
FIGS. 22A and 22B show aspects of an embodiment of the invention, which aspects comprise a laser (1), an iris (4), an eye (5), and a computer guided tracking system (20).
Figure 22B:
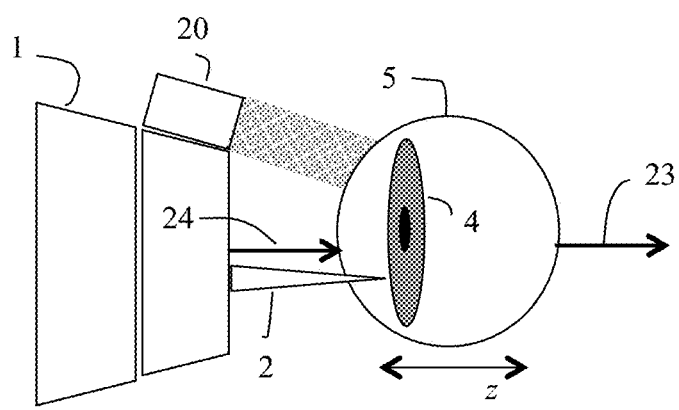
Figure 23:
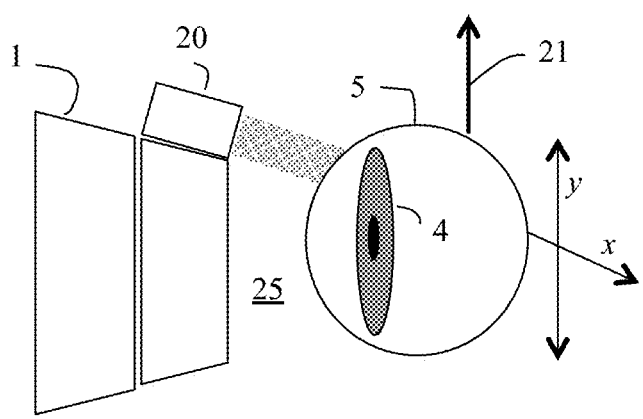
FIG. 23 shows aspects of an embodiment of the invention, which aspects comprise a laser (1), an iris (4), an eye (5), and a computer guided tracking system (20), wherein the computer guided tracking system (20) has detects movement (21) of the eye (5) along the x-y plane and interrupts (25) the laser beam (2).
Figure 24:
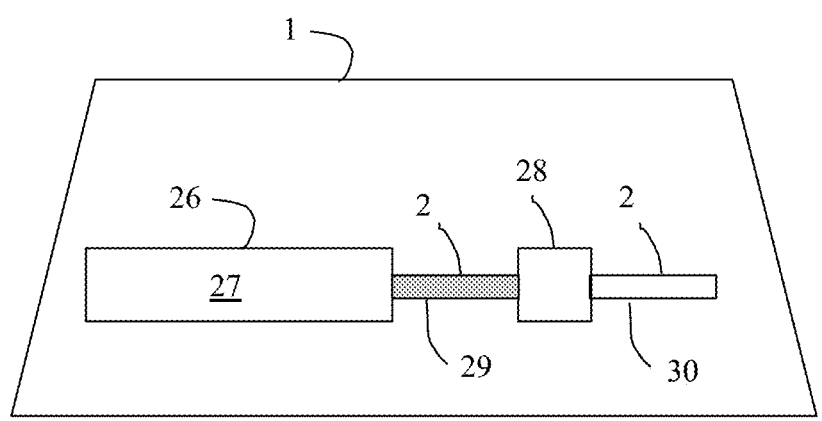
FIG. 24 shows aspects of an embodiment of the invention, which aspects comprise a laser (1), a laser gain (26), a laser beam (2), and a harmonic doubler (28), wherein the laser gain (26) comprises an Nd:YAG medium (27), and the laser radiation is generated by the laser gain at its natural harmonic (with a wavelength of 1064 nm) (29) and from the harmonic doubler (28) at its second harmonic (with a wavelength of 532 nm) (30).

In another embodiment, the spot is a torus shape, with an inside diameter of 3.5 mm to accommodate the pupil and an outer diameter of 11 mm to cover the patient's entire iris. See FIG. 7. The beam remains stationary through the treatment. In another version of the foregoing embodiment, a continuous-wave Nd:YAG laser (1064 nm) laser is used. In another version of each of the foregoing embodiment, the TM and/or the UM is treated. In another version, neither the TM nor the UM is treated. In yet another version, the pupillary zone is treated. (The pupillary zone is the area of the iris inside the collarette. See FIG. 8.) And in another version, the pupillary zone is not treated. See FIG. 9. In still another version, the peripheral iris is treated, and in another it is not.

In yet another embodiment of the invention, a Q-switched, argon-pumped tunable dye (APTD) laser (577/585 nm) is used. The pulse width is 10 ps, the spot size is d=50μ, and the spot and line separation are 100μ, placing one full spot diameter between each spot along both x and y. The spared tissue between spots aides healing, and the narrower pulse width isolates tissue damage closer to the spot diameter. The patient returns in two weeks for a second treatment and in another two weeks for a third treatment before IOP is reduced to normal levels.

In another embodiment of the invention, the approximate frequency of the laser output is between about 300 nm and about 2000 nm, and the approximate energy density at the anterior iris is between about 0.45 J/cm^2 and about 2.0 J/cm^2.

One example of the use of the invention is as follows: An adult, brown-eyed male patient presents with closed-angle glaucoma in OD. The drainage angle is 15%, and the patient's IOP is about 42 mm Hg. Pupillometry indicates a pupillary diameter of 4 mm. The patient is otherwise found in satisfactory general and ocular health. After being counseled regarding the procedure, a topical anesthetic (lidocaine hydrochloride) and a miotic solution (pilocarpine) are instilled into OD. Thirty minutes later, the patient's head is stabilized, and OD is treated with a Q-switched, frequency-doubled Nd:YAG laser. The laser produces a circular spot with a diameter of 120μ and an energy density of 1.0 J/cm^2. The beam divergence is 17%. The pulse width is 20 ns. The laser is computer-guided in a spiral scan pattern across the entire iris. The spiral begins along the circumference of the pupil and spreads to the outer periphery of the iris. Both the spot and line separation are 180μ (i.e., 60μ between spots along both x and y). The repetition rate is 5 kHz, and the beam is maintained at a perpendicular angle to the iris throughout the procedure. The scan is repeated 12 times. Computer-guided tracking is used to follow the eye in the x, y, and z directions and interrupt transmission if the patient's head or eye moves during treatment. Neither the TM nor the uveal meshwork is treated. Immediately post-op, the patient's IOP falls to 23 mm Hg.

The patient returns the following day for a follow-up exam. The IOP has fallen further to 20 mm Hg. In addition, the patient's pupil measures d=5 mm suggesting further refraction of the iris tissue. As the pupillary constrictor muscles adapt, they can be expected to restore the pupil to its normal size, thereby creating additional iris tissue refraction and greater tension on the TM and uveoscleral pathways.

One of ordinary skill in the art would recognize many other variations, modifications, and alternatives. The above examples are merely illustrations, which should not unduly limit the scope of the claims herein. It is also understood that the examples and embodiments described herein are for illustrative purposes only and that various modifications or changes in light thereof will be suggested to persons skilled in the art and are to be included within the spirit and purview of this application and scope of the appended claims.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method for reducing intraocular pressure in an eye, comprising applying laser radiation in the form of a laser beam to at least approximately an entire anterior surface of an iris of the eye, wherein stromal pigment resides on the anterior surface, wherein a frequency of the laser radiation is such that the laser beam is capable of passing through a cornea of the eye, wherein the frequency of the laser radiation is such that the stromal pigment serves as a chromophore for the laser beam, wherein an energy density of the laser radiation is such that the laser radiation induces retraction in least a portion of iris tissue, wherein the retraction induces at least one of the following:
   a reduction in a convexity of the iris,
   an enlargement of a drainage angle of the eye,
   an increase in aqueous outflow through a trabecular meshwork of the eye,
   an increase in aqueous outflow through a uveoscleral pathway of the eye,
   a reduction in contact between zonule fibers of the eye and a pigment epithelium of the iris, and
   an increase in the area between a pupil of the eye and an anterior lens capsule of the eye.

2. The method of claim 1, further comprising applying the laser radiation to the anterior surface utilizing a computerized scanning system, configured to scan the laser beam throughout the at least approximately entire anterior surface of the iris.

3. A system for reducing intraocular pressure in an eye, wherein stromal pigment resides on an anterior surface of the eye, comprising:
   a laser, wherein the laser is configured to apply laser radiation in the form of a laser beam to at least approximately an entire anterior surface of an iris of the eye, wherein a frequency of the laser radiation is such that the laser beam is capable of passing through a cornea of the eye, wherein the frequency of the laser radiation is such that the stromal pigment serves as a chromophore for the laser beam, wherein an energy density of the laser radiation is such that the laser radiation induces retraction in least a portion of iris tissue, wherein the retraction induces at least one of the following:
   a reduction in a convexity of the iris,
   an enlargement of a drainage angle of the eye,
   an increase in aqueous outflow through a trabecular meshwork of the eye,
   an increase in aqueous outflow through an uveoscleral pathway of the eye,
   a reduction in contact between zonule fibers of the eye and a pigment epithelium of the iris, and
   an increase in the area between a pupil of the eye and an anterior lens capsule of the eye;
a computerized scanning system, configured to scan the laser beam throughout the at least approximately entire anterior surface of the iris.

4. The method of claim 1, further comprising tracking movement of the eye in at least one of the x, y, and z directions, utilizing a computer guided tracking system configured to detect the movement, and at least one of:
   adjust the position of the laser beam to follow the movement throughout the at least approximately entire anterior surface of the iris, or
   interrupt transmission of the laser beam.

5. The system of claim 3, further comprising a computer guided tracking system, configured to detect movement of the eye in at least one of the x, y, and z directions, and at least one of:
   adjust the position of the laser beam to follow the movement throughout the at least approximately entire anterior surface of the iris, or
   interrupt transmission of the laser beam.

6. The method of claim 1, wherein the laser comprises an Nd:YAG gain medium.

7. The method of claim 1, wherein the laser is configured to generate laser radiation in the infrared spectrum.

8. The method of claim 1, wherein the laser is configured to generate a laser beam with a pulse width in the nanosecond range.

9. The method of claim 1, wherein the laser is configured to generate a laser beam with a pulse width in the microsecond range.

10. The system of claim 3, wherein the laser comprises an Nd:YAG gain medium, and the laser radiation is tuned using at least one of its natural harmonic (with a wavelength of 1064 nm) or its second harmonic (with a wavelength of 532 nm).

11. The system of claim 3, wherein the laser is configured to generate laser radiation in the infrared spectrum.

12. The system of claim 3, wherein the laser is configured to generate a laser beam with a pulse width in the nanosecond range.

13. The system of claim 3, wherein the laser is configured to generate a laser beam with a pulse width in the microsecond range.

* * * * *